United States Patent [19]
Treace

[11] 4,193,140
[45] Mar. 18, 1980

[54] KNEE PROSTHESIS

[75] Inventor: Harry T. Treace, Forest Hill, Tenn.

[73] Assignee: Richards Manufacturing Company, Inc., Memphis, Tenn.

[21] Appl. No.: 642,369

[22] Filed: Dec. 19, 1975

[51] Int. Cl.² .................................................. A61F 1/24
[52] U.S. Cl. .................................. 3/1.911; 128/92 C
[58] Field of Search ........................... 3/1.9–1.913, 3/1; 128/92 C, 92 CA

[56] References Cited

U.S. PATENT DOCUMENTS

| | | | |
|---|---|---|---|
| 2,679,245 | 5/1954 | Timmermans | 128/92 CA |
| 3,528,109 | 9/1970 | Scales | 3/1.91 |
| 3,715,763 | 2/1973 | Link | 3/1.911 |
| 3,774,244 | 11/1973 | Walker | 3/1.911 |
| 3,837,009 | 9/1974 | Walker | 3/1.911 |
| 3,839,742 | 10/1974 | Link | 3/1.91 |
| 3,852,830 | 12/1974 | Marmor | 3/1 |
| 3,868,730 | 3/1975 | Kaufer et al. | 3/1 |

FOREIGN PATENT DOCUMENTS 426096 6/1967 Switzerland ............................ 3/1.912

Primary Examiner—Ronald L. Frinks
Attorney, Agent, or Firm—John R. Walker, III

[57] ABSTRACT

Knee prosthesis for permitting total or partial replacement of an articulating portion or portions of the knee. The knee prosthesis is particularly adapted for attachment to one of the condyles of the knee, and includes a curved elongated body portion, a post fixedly attached to the body portion, and a plurality of cement holding rings attached to the body portion.

2 Claims, 10 Drawing Figures

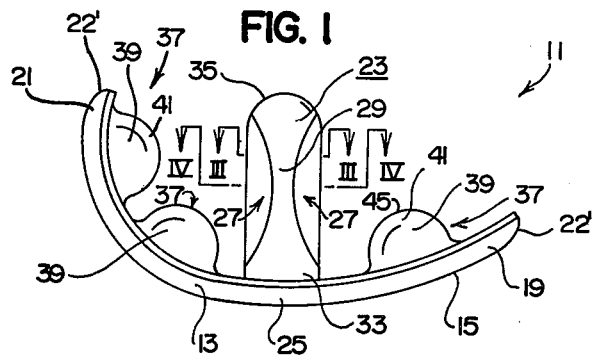

KNEE PROSTHESIS

BACKGROUND OF THE INVENTION

1. Field of the Invention

This invention relates to the field of prostheses for the human knee.

2. Description of the Prior Art

During the use of the human knee there are many forces that act thereon, particularly during walking, running, or jumping. For example, in stepping down from a curb or jumping, the impact forces of the foot against the street or other surfaces are transmitted through the leg and the knee. Thus, these forces act on a knee prosthesis applying various forces, such as impact and tension forces, tending to cause the problem of loosening the prosthesis from the bone particularly over a period of time after the continual application of such forces. Also, for example, an impact or a compression force on one end of a prosthesis, i.e., either the anterior or the posterior end portion, would tend to cause a rocking of the prosthesis about its central portion and have the opposite effect on the other end. For example, an impact force acting on the anterior end of the prosthesis would tend to cause a tension pull-out force on the posterior end, and vice versa. In addition, there is the problem in prostheses with sharp edges on portions thereof to have a tendency to cut or crack the cement that has been provided to cement the prosthesis in place in the bone. Additionally, there are some other forces acting on the prosthesis, such as twisting forces, although these are minimal as compared with the impact and tension forces, and if a flat tibial plateau prosthesis is used it is of practically no consequence.

Heretofore, there have been various prostheses for use as the femoral component. Applicant has knowledge of a number of them, which have been patented. Some of these prior art devices are as follows: U.S. Pat. Nos. 3,852,830; 3,715,763; 3,728,742; and 3,774,244; German Pat. No. 939,226 and Italian Pat. No. 498,150. None of these patents disclose or suggest the improved prosthesis of the present invention.

SUMMARY OF THE INVENTION

The present invention is directed toward overcoming the heretofore mentioned and other problems by providing a highly effective knee prosthesis which has a post that serves a threefold purpose, namely: (1) providing means for resisting impact forces, (2) providing means for resisting pull-out tension forces and (3) providing means for resisting any and all twisting forces that might be encountered; and which prosthesis has cement holding rings along the curved body portion of the prosthesis that serve a twofold purpose, namely: (1) providing means spaced along the body portion for resisting pull-out tension forces and (2) resisting impact forces. Additionally, the present invention provides a knee prosthesis which is adapted to be made with a relatively thin body portion so that a minimum amount of bone may be removed. Also, the present invention provides a knee prosthesis that is effective to resist cutting or cracking of the anchoring cement.

The means by which the foregoing and other objects and advantages of the present invention are accomplished are as follows:

The knee prosthesis of the present invention includes a curved elongated body portion, a post means fixedly attached to the body portion intermediate the posterior and anterior ends of the body portion, and a plurality of cement holding rings disposed along the body portion. The post is substantially cross-shaped in cross section and provides a means in and of itself for resisting any and all twisting forces which might be encountered. Also, the post is blunt on the end for resisting impact forces acting on the prosthesis, and the cross-shaped cross section is larger adjacent the top of the post than portions therebelow so that the post resists tension pull-out forces. The cement holding rings are blunt on the outer ends thereof to resist impact forces and are enlarged to resist pull-out tension forces. Also, the cement holding rings are semicircular and are provided with fillets at the forward and rearward junctures of the rings with the body portion to prevent cutting and cracking of the anchoring cement by the cement holding rings.

DESCRIPTION OF THE DRAWINGS

FIG. 1 is a side elevational view of the knee prosthesis of the present invention.

FIG. 2 is a top plan view thereof.

FIG. 3 is an enlarged sectional view taken as on the line III—III of FIG. 1.

FIG. 4 is an enlarged sectional view taken as on line IV—IV of FIG. 1.

FIG. 5 shows a fragmentary portion of one of the condyles of the knee shown prepared to receive the knee prosthesis of the present invention.

FIG. 6 is a view similar to FIG. 5 but showing an alternate method of preparation of the condyle to receive the prosthesis of the present invention.

FIG. 7 is a sectional view taken along the longitudinal center line of the prosthesis of the present invention showing the prosthesis embedded in a condyle of the knee and with the anchoring cement in place.

FIG. 8 is an enlarged sectional view taken as on the line VIII—VIII of FIG. 7.

FIG. 9 is a sectional view taken as on the line IX—IX of FIG. 7.

FIG. 10 is a sectional view taken as on the line X—X of FIG. 9.

DESCRIPTION OF THE PREFERRED EMBODIMENT

The prosthesis 11 of the present invention comprises a body portion 13 having a lower surface 15 and an upper surface 17. For purposes of identification the body portion 13 is divided into two sections or ends, namely an anterior end 19 and a posterior 21. As viewed from the side (FIG. 1), body portion 13 is curved along its length. Lower surface 15 is preferably polycentric, that is, the surface lies in arcs of circles having more than one center and more than one radius to approximate the natural articulating surface of a condyle of the femur. As best seen in FIG. 1 the lower surface 15 in the anterior end 19 curves somewhat gradually and the posterior end 21 curves relatively sharply. In other words, the radius of an imaginary circle in which the anterior end 19 lies is substantially greater than the radius of the imaginary circle in which the posterior end 21 lies.

Body portion 13 is relatively thin, as will be seen in FIG. 10, and can be so made due to the unique construction which will be more apparent in the description to follow. This is in contrast to some of the previous femoral components which have been relatively thick, thereby necessitating the removal of either more bone into which the curved body portion is recessed or, in the alternative, necessitating the body portion extending beyond the face of the condyle, depending upon the surgical technique utilized. On the other hand, with the curved body portion of the present invention being relatively thin the depth of the recessed cutout can be reduced. Also, as will be seen in FIG. 10 the upper surface 17 of body portion 13 is straight as viewed in transverse cross section and the lower surface 15 is arcuate with the thicker portion being adjacent the center of the body portion 13 and curving symmetrically upwardly in opposite directions to the terminations thereof at the opposite side edges 22 of body portion 13, which as will be seen in FIG. 10 are very thin. The cross section of body portion 13 is substantially the same throughout the length thereof and as shown in FIGS. 8 and 10, except that the corners of the body portion 13 are preferably rounded as at 13', and the side edges 22 and ends 22' of the body portion 13 are on a radius.

Body portion 13 is rigid, as for example, it is preferably made of stainless steel which has been micro-finished on the lower surface 15 thereof, or if desired may be made of any other suitable material, as for example chrome cobalt.

Prosthesis 11 includes a post 23 which is fixedly and preferably integrally attached to the curved body portion 13 intermediate the anterior end 19 and the posterior end 21 and preferably centrally of body portion 13, that is, along the longitudinal center line thereof and in the vicinity of a place substantially halfway between the anterior and posterior ends 19, 21. Post 23 extends upwardly from the upper surface 17 in a direction remote from lower surface 15 and substantially perpendicular to the intermediate portion 25 of body portion 13. As viewed from the top as in FIGS. 2, 3, and 4 the outer surface 24 of post 23 preferably lies in an imaginary circle and is cut out as at 27 on four sides thereof (at 90° intervals) to establish a crosslike cross section, as best seen in FIGS. 3, 4 and 9 which provide four armlike portions 29 respectively between the cutout portions 27 and which emanates spoke-like from the central portion 31 of the post 23. As will be seen from FIG. 1 each of the cutout portions 27 is arcuate with the deeper portion being intermediate the lower end 33 of post 23 and the top 35 of the post 23 to establish a reduced central portion 31' which is smaller than the central portion 31" thereabove and the top 35. Also, this causes the parts 29' of the armlike portions 29 emanating from the reduced central portion 31' to be narrower than the parts 29" of the armlike portions 29 emanating from the central portion 31" which is above central portion 31'. With this unique configuration of post 23 there is accomplished a threefold purpose, as will be better understood in the description to follow later in the specification of the use of the prosthesis 11. In addition, it should be pointed out that top 35 is blunt, as best seen in FIGS. 1, 7 and 10, for a purpose later to be described.

A plurality of cement holding rings 37 are fixedly and preferably integrally attached to body portion 13 and extend generally upwardly from upper surface 17 thereof. There are preferably, though not necessarily, two of rings 37 between post 23 and the posterior end 21 and preferably, though not necessarily, one ring 37 between the post 23 and the anterior end 19 thereof. Cement holding rings 37 are preferably aligned in an imaginary plane extending fore and aft along the center line of body portion 13 and are preferably in spaced relationship to each other and to post 23.

Each of the cement holding rings 37 are preferably of similar construction, and the following description of one will suffice for all. Cement holding ring 37 is preferably semi-circular when viewed from the side, as in FIG. 1, and the opposite sides thereof are preferably dished out as at 39 to provide an enlarged semi-circular ringlike outer portion 41, which is preferably blunt along the outer surface, as at 43, and to provide a reduced portion 45 connecting outer portion 41 with body portion 13. The distance from the base 37' of ring 37 to the blunt outer surface 43 at the highest point or apex 45 of ring 37 is preferably substantially less than the top 35 or height of post 23. In addition, at the forward and rearward junctures of ring 37 with body portion 13 are provided fillets 47, 49 (FIG. 7) respectively. Fillets 47, 49 prevent any cutting action into the cement as might otherwise occur if the holding ring 37 had a straight side and was not rounded.

From the foregoing, it will be apparent that prosthesis 11 is preferably of one piece construction and preferably formed of stainless steel, or other suitable material. The prosthesis 11 is preferably provided in several sizes to accommodate different sizes of femurs.

In the use of the prosthesis 11 of the present invention, it may be implanted in the femur F of a human knee by methods well known to those skilled in the art in implanting other types of femoral components, and may be utilized in one or both compartments of the knee, that is, either or both of the medial or lateral compartments of the knee. Also, it may be utilized with suitable tibial components well known to those skilled in the art, as for example, with a tibial component formed of ultrahigh molecular weight polyethylene having a surface engagable by lower surface 15, and which surface preferably, although not necessarily, is flat or substantially so in which case there is substantially no twisting forces present during normal use on the femoral component.

FIG. 5 shows one method of preparing the femur F by drilling a cylindrical bore B into the femur and drilling a pair of slots S, S' extending outwardly from the bore B. It will be understood that the bore B receives the post 23 and the slots S, S' receive the cement holding rings 37 with cement C being placed in the slots S, S' and bore B. The cement is of any suitable type, and preferably of the acrylic bone cement type well known to those skilled in the art.

FIG. 6 shows an alternate method of preparation of the femur F in which the bore B is separate from the slot S and the slot S'. In this case, it will be understood that the two posterior rings 37 shown in FIG. 7 are received in the slot S and the one anterior ring 37 is received in the slot S'. In FIG. 7 the prosthesis 11 is shown in place in the femur F which has been prepared in accordance with the method shown in FIG. 5 and the cement C is shown in the slots S, S' and bore B. It will be appreciated that the post 23 of the prosthesis 11 of the present invention provides a safety factor in the event that the surgeon inadvertently does not provide sufficient cement in the slots S, S', but does include cement under the body portion 13 as is customary in such procedures. This safety factor is possible since the post 23 performs all of the following primary functions:

(1) The cement C acting against the enlarged head or top 35 of post 23 anchors the prosthesis against pull-out tension forces acting downwardly as shown by the arrow 51.

(2) The blunt top 35 acting against the cement and the end E of the bore B acts to resist impact forces in the direction shown by the arrow 53.

(3) The armlike portions 29 coact with the cement to prevent twisting of the prosthesis 11 about the longitudinal axis of post 23.

Thus, synergistic results are accomplished by means of a single post which is of the above unique construction and which has the outer surface thereof lying in an imaginary circle so that the post will fit into a bore made, as for example, by a drill bit whereby a minimum amount of bone can be removed and yet the above results obtained while at the same time there are no sharp cutting edges to cut or crack the cement. In fact, the assignee has made twisting tests with the rings 37 removed and the failure occurred by the twisting of the metal of post 23 before any breakdown of the cement occurred and way beyond any twisting forces ever expected to be encountered. Similarly, impact and tension pull-out tests were made which gave results far beyond any such forces expected to be encountered during the use of the prosthesis 11. Also, the benefits of the cement holding rings 37 can be appreciated when it is realized that a thin body portion 13 may be utilized since the rings anchor the body portion along the length thereof at spaced places to prevent any impact or pull-out tension forces which might otherwise cause a bending of the body portion if the rings 37 were not present. It previously was necessary to have a suitable geometric design of the body portion of the prosthesis to prevent bending of the body portion, as for example, by having the body portion and/or the edges thick. It will be appreciated also that the enlarged ringlike outer portion 41 having a blunt outer surface 43 resists impact or pull-out tension forces acting on the body portion adjacent the ring 37. For example, it will be apparent that an impact or compression force acting in the direction of the arrow 55 (FIG. 7), if it were not for the rings 37 and the improved post 23 of the present invention, would cause a force tending to pivot the body portion 13 counterclockwise as viewed in FIG. 7 about the post 23 and cause a pull-out force as shown by the arrows 57 in FIG. 7 which would tend to loosen the prosthesis 11 from the cement. However, with the cement holding rings 37 of the present invention it will be understood that the compression force at the arrow 55 is resisted by the blunt edge 43 acting against the bottom 59 of the slot S' or against the cement adjacent the bottom 59. Also, it will be understood that the enlarged outer portion 41 of the rings 37 on the posterior end acting against the cement C in the slot S will resist the pull-out tension forces acting as shown by the arrows 57.

Although the invention has been described and illustrated with respect to a preferred embodiment thereof, it is to be understood that it is not to be so limited since changes and modifications may be made therein which are within the full intended scope of the invention.

I claim:

1. A knee prosthesis for implanting with cement in a human knee comprising:
 (a) a single curved elongated body portion having upper and lower surfaces, and having posterior and anterior ends;
 (b) single post means fixedly attached to said curved body portion intermediate said posterior and anterior ends and extending generally upwardly from said upper surface for interaction with the cement with which used to resist in and of itself all twisting forces which might be encountered in the use of the prosthesis and to resist tension and compression forces, said post means in cross section along a substantial portion of the length thereof is cross shaped and said post means is of a reduced size in cross-sectional area at a midportion halfway between the upper and lower ends thereof, and with said post means increasing in cross-sectional size from said midportion towards said upper and lower ends; and
 (c) at least one cement holding means of less height than said post, fixedly attached to said body portion and extending in a direction generally remote from said lower surface for interaction with the cement with which used to provide support to said body portion and to resist tension and compression forces along a substantial portion of the length of said body portion.

2. A knee prosthesis for implanting with cement in a human knee, comprising:
 (a) a curved elongated body portion having upper and lower surfaces, and having posterior and anterior ends;
 (b) a post fixedly attached to said curved body portion intermediate said posterior and anterior ends and extending generally upwardly from said upper surface, said post in cross section along a substantial portion of the length being cross-shaped for preventing rotation of said curved body portion during use when implanted in a knee with cement;
 (c) a plurality of cement holding rings fixedly attached to said body portion, said rings extending generally upwardly from said upper surface, said rings being disposed in spaced relationship with one another and said post, and being disposed along the length of said body portion intermediate said posterior and anterior ends, each of said rings extending forwardly and rearwardly towards the anterior and posterior ends of said body portion and including forward and rearward junctures with said body portion, each of said rings including fillets respectively at said forward and rearward junctures, each of said rings including an enlarged ringlike means and a reduced portion smaller than said enlarged ringlike means connecting said enlarged ringlike means with said body portion for anchoring against tension forces said body portion to a knee in which implanted with cement and for resisting compression forces on said body portion.

* * * * *